United States Patent
Segal

(10) Patent No.: US 6,666,686 B2
(45) Date of Patent: *Dec. 23, 2003

(54) DENTAL ANCHORING DEVICE

(76) Inventor: Alan Julian Segal, 13 Park Ave., Hale, Cheshire WA15 9DL (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 07/828,933
(22) PCT Filed: Jul. 23, 1990
(86) PCT No.: PCT/GB90/01130
  § 371 (c)(1),
  (2), (4) Date: Sep. 14, 2000
(87) PCT Pub. No.: WO91/01693
  PCT Pub. Date: Feb. 21, 1991

(65) Prior Publication Data

US 2003/0157462 A1 Aug. 21, 2003

(30) Foreign Application Priority Data

Aug. 3, 1989 (GB) ............................................... 8917772
Feb. 10, 1990 (GB) ............................................... 9003046

(51) Int. Cl.$^7$ ................................................. A61C 5/04
(52) U.S. Cl. ...................................... 433/225; 433/165
(58) Field of Search ............................... 433/225, 165, 433/166

(56) References Cited

U.S. PATENT DOCUMENTS

| 3,995,372 | A | * | 12/1976 | Rapuano | 433/225 |
|---|---|---|---|---|---|
| 4,083,115 | A | | 4/1978 | McKelvey | |
| 4,202,101 | A | * | 5/1980 | Weissman | 433/225 |
| 4,219,620 | A | | 8/1980 | Carse | 433/225 |
| 4,480,998 | A | * | 11/1984 | Carse | 433/225 |
| 4,553,942 | A | * | 11/1985 | Sutter | 433/225 |
| 4,579,531 | A | | 4/1986 | Hinks | 433/225 |
| 4,655,711 | A | * | 4/1987 | Weissman | 433/225 |

FOREIGN PATENT DOCUMENTS

GB   1482681   8/1977

* cited by examiner

Primary Examiner—John J. Wilson
(74) Attorney, Agent, or Firm—Pearson & Pearson, LLP

(57) ABSTRACT

A dental anchoring device for attaching to a dentist's drill bit comprises a threaded anchoring part, connected to a rod by a weakened waisted portion. The rod is carried by a main body of the dental anchoring device with a shaped axial blind bore for fitting the body onto the shank of the drill bit, having a bit end receivable in the blind bore. A tapered part of the shank of the drill bit and matching section of the bore are provided with respective flat faces to key the shank to the body. A locking groove keys the shank of the drill bit into the chuck of a dentists drill. In an alternative embodiment, a line of weakness is provided between a metal anchoring rod and a plastics body, which is severed when a limiting torque is exceeded, allowing the body to be withdrawn, and the rod to be left in situ.

20 Claims, 1 Drawing Sheet

DENTAL ANCHORING DEVICE

TECHNICAL FIELD

This invention relates to a device for use in dentistry to anchor a superstructure to a tooth understructure.

BACKGROUND ART

It has long been known to insert screws into pre-drilled holes in tooth structures to provide anchors for artificial superstructures. Originally this was done with a length of threaded rod which was screwed by hand into a pre-drilled bore using a shaped grip at the end of the rod. Surplus projecting rod was then cut off.

UK patents 1347226 and 1347227 described the use of a threaded rod having a point of weakness between a threaded anchoring part and a gripping part. The rod is fully screwed into a pre-drilled bore and further screwing action then causes the gripping part to be severed from the anchoring part.

In 1347226 two points of weakness are provided to give different lengths of anchoring parts, and the gripping part has a shank adapted to fit into a special chuck attachment for a conventional dentist's drill.

In 1347227, there is one point of weakness, an anchoring head is provided on the threaded part, and the gripping part has a shank adapted to fit into a hand tool comprising a knurled knob which can be gripped between the fingers.

UK patent 1482681 describes a threaded rod having an integral shank with a point of weakness therebetween. The shank is shaped to fit directly into a conventional dentists drill (i.e. without requiring a special chuck or adaptor).

U.S. Pat. No. 4,202,101 describes one or two part dental anchors with wings formed on their ends, and a shank with an axial blind bore in which the winged end is inserted, the other end of the shank being adapted for driving connection to a chuck of a dental drill.

U.S. Pat. No. 4,155,162 describes a two part dental anchor with an L-shaped free end, for engaging in notches in a longitudinal slot in a cylindrical body, giving alternative extensions of the anchor from the body as the parts of the anchor are used in turn; U.S. Pat. No. 4,053,982 is related to this, disclosing a one, two or three sectioned dental anchor also with an L-shaped free end for engaging in a single notch in a cylindrical coupling body.

GB 1528245 describes a dental hand wrench, with a handling end portion, a cylindrical body, and a threaded pin connected to the body by a wasted portion so that the pin can be separated from the body after being normally screwed into a substrate.

It is convenient to be able to use the dentists drill to screw the anchoring device into the tooth. However, the above mentioned prior art arrangements which have this feature necessitate some modification or manipulation of the drill. Thus, with the arrangement of GB 1347226 it is necessary to fit a special chuck to the drill. With the arrangement of GB 1482681, although a special chuck is not required it is necessary to remove the drill bit and fit the shank of the anchoring device in place of the drill bit.

DISCLOSURE OF INVENTION

An object of the present invention is to provide an anchoring device which can be used with a dentist's drill in a particularly convenient manner.

According to one aspect of the invention therefore there is provided a dental anchoring device comprising a threaded anchoring part, a connecting part adapted for detachable drivable connection to a dentist's drill, and at least one position of weakness between the anchoring part and the connecting part, characterised in that the connecting part is adapted to be connected to the drill with a drill bit in the drill.

With this arrangement, conveniently the anchoring device can be connected to the drill after the drill has been used with a drill bit to drill a bore for the anchoring device in a tooth, without need for the drill bit to be removed. The threaded anchoring part can then be driven into the pre-drilled bore using the drill. Once the anchoring part is fully inserted the connecting part can be removed in conventional manner by severing at the position of weakness caused by further rotation of the connecting part by the drill. The severed connecting part can then be removed from the drill and discarded leaving the drill bit ready for further use.

With regard to the threaded part this may be a threaded metal rod which may be generally of conventional form. The position of weakness may be a waisted or cut away portion between the threaded rod and the adjacent portion of the connecting part. The rod, the waisted or cut-away portion and the adjacent portion may be formed in one piece.

According to a second aspect of the invention, there is provided a dental anchoring device comprising a threaded anchoring part, and a connecting part adapted for detachable driving connection to a dentist's drill, the connecting part being drivably interconnected to the anchoring part so as to be releasable therefrom when a predetermined level of driving torque is exceeded characterised in that the connecting part is interconnected with the anchoring part by a structure which is adapted to rupture or deform circumferentially to permit said release thereof when said level of driving torque is exceeded.

Preferably said connecting part is adapted to be connected to the drill with a drill bit in the drill in accordance with the first aspect of the invention.

With regard to the rupturable or deformable structure, preferably this is achieved by drivable interconnection between relatively strong and weak parts, particularly between metal and plastics parts, so that the weaker part preferentially ruptures or deforms. Alternatively or additionally the drivable interconnection may be achieved between parts which are bonded or welded or similarly fixed together so that the bond or weld or other joint is preferentially ruptured.

In a particularly preferred embodiment the threaded anchoring part comprises a rod which is threaded at one end, and the connecting part comprises a plastics body which is moulded around the other end of the rod. The said other end of the rod may be appropriately configured, e.g. by provision of one or more 'flats', to drivably key the rod circumferentially to the plastics body.

With the first aspect of the invention, and the second aspect when combined with the first aspect, the connecting part may have a receptacle in a body thereof to receive the drill bit. This may comprise an axial bore or the like whereby the body is generally of tubular construction having solid or open-work side walls. This body may be formed integrally in One piece with the above mentioned adjacent portion or may be a separate part fixed thereto (and may be formed from metal or plastics).

For detachable drivable connection relative to the drill the connecting part may incorporate a circumferential locking structure which incorporates elements to prevent rotation relative to the drill and/or a longitudinal locking structure which incorporates elements to restrict longitudinal separation from the drill.

Thus, the connecting part may have side abutment faces or the like which engage corresponding side abutment faces of the drill bit to prevent relative rotation. Conveniently, the former flat faces may be provided in the above mentioned axial bore.

The connecting part may have a deflectable abutment structure which makes a releasable snap fit to restrain longitudinal movement relative to the drill.

With reference to the connection between the anchoring device and the drill it is to be understood that this may take place directly, i.e. by interengagement between the anchoring device and the drill chuck, or indirectly i.e. by interengagement between the anchoring device and the drill bit as more particularly described above. Most preferably the latter arrangement is adopted and the interengagement is preferably effected with a shank part of the drill bit. Whatever drive connection is adopted this should most preferably be such as to permit ready attachment to give positive drive interconnection, and also to permit ready release so that, after use, the device can be conveniently removed to free the drill, and the drill bit for use.

With regard to the drill, this may be any suitable powered dentist's drill or hand tool; and the bit may be any suitable kind of drill bit of twist or other form.

BRIEF DESCRIPTION OF DRAWINGS

The invention will now be described further by way of example only and with reference to the accompanying drawings in which.

MODES FOR CARRYING OUT THE INVENTION

Figure 1:
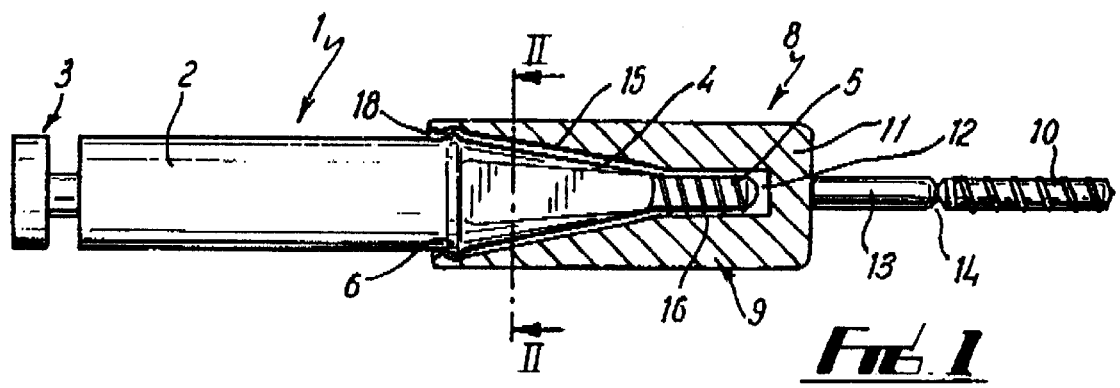
FIG. 1 is a diagrammatic partially sectional view of one form of an anchoring device according to the invention mounted on a dentist's drill bit.
Figure 2:
FIG. 2 is a cross-section on line II—II of FIG. 1.

FIGS. 1 and 2 of the drawings show a dentist's drill bit 1 of generally conventional form having a cylindrical shank 2 terminating at one end in a conventional locking structure 3 for engaging the chuck of a dentist's drill (comprising a part annular groove and a flat face). At the other end, the shank 2 has a tapered portion 4 and an axially extending twist drill bit 5. The shank 2, tapered portion 4 and drill bit 5 define an integral construction which may be made in one or more pieces.

There is a slightly raised circumferential ridge 6 between the tapered portion 4 and the shank 2, and the tapered portion 4 has one or more flat faces 7 thereon (two are illustrated).

The drawings also show an anchoring device 8 having a connection part 9 and an anchoring part 10.

The connection part 9 has a main body 11 which is of generally cylindrical form with a shaped blind bore 12 extending axially from one end of the body 11. The other end of the body 11 has an integral rod 13 extending axially thereof.

The rod 13 is formed from metal in one piece with the anchoring part 10 which is also in the form of a rod. Both rods 10, 13 are cylindrical, the outer surface of the rod 13 being smooth and wholly axially parallel, and the outer surface of the rod 10 having a regular screw thread extending throughout its entire length but otherwise having an axially parallel outer surface. The maximum diameters of the rods 10, 13 are identical and between the two rods 10, 13 there is a linking portion 14 which is waisted or cut away with a circumferential groove to define a position of weakness.

The bore 12 in the body 11 is shaped to provide a section 15 at the open end of the bore 12 tapering inwardly, and a cylindrical section 16 extending axially from the small end of the section 15 to the blind end of the bore 12. As shown in the drawings, the bore 12 is shaped to fit snugly over and around the drill bit 5 and the tapered portion 4 and accordingly, the length and diameter of the section 16 correspond to the drill bit 5 and the dimensions and shape of the section 15 correspond to the tapered portion 4 (whereby, as shown, the inner surface of the section 15 has two flat faces 17 thereto).

On the inner surfaces of opposite parts of the wider end of the section 15 there are deformable projections 18 which coact with the raised ridge 6 to form a releasable snap fit.

Conveniently, the body 11 may be formed from plastics and may be moulded onto (or firmly push-engaged with) the rod 13.

With the above arrangement, in use, a tooth stump or the like is pre-drilled with a blind bore using the drill bit 1 fitted in a conventional dentist's drill.

The anchoring device 8 is then pushed over the drill bit 1 with the flat faces 17 of the section 15 aligned with the flat faces 7 of the tapered portion 4 until the projections 18 snap-fit over the ridge 6.

The anchoring device 8 is thereby held securely in position in that it cannot rotate relative to the bit 1 and it cannot fall longitudinally therefrom.

The threaded rod 10 is then screwed into the pre-drilled bore using the drill (via the drill bit 1). When the rod 10 is fully inserted the anchoring device 8 severs at the position of weakness 14 leaving the threaded rod 10 fixed securely in the tooth and projecting therefrom. The remaining part of the anchoring device (i.e. the connecting part 9 comprising the body 11 and the rod 13) can then be pulled off the bit 1 and discarded. The bit 1 can then be used as required.

With this arrangement the inconvenience of having to remove the bit 1 to use the drill to insert an anchoring device 8 is avoided.

Figure 3:
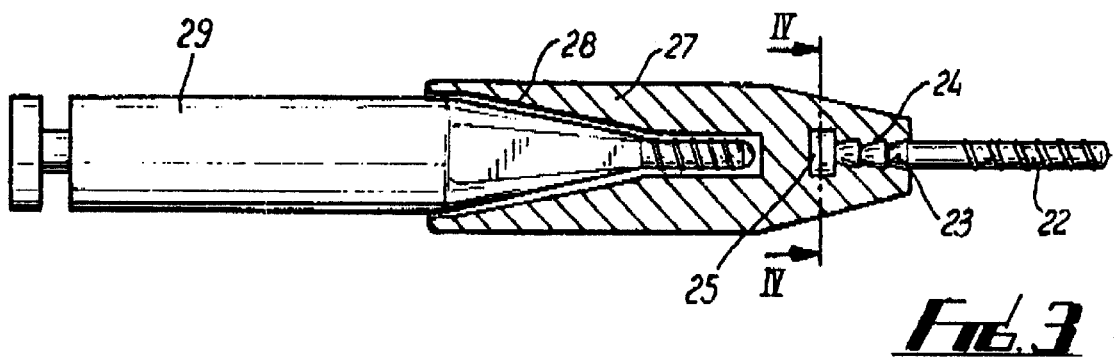
FIG. 3 is a view similar to FIG. 1 of a second form of anchoring device according to invention mounted on a dentist's drill bit.
Figure 4:
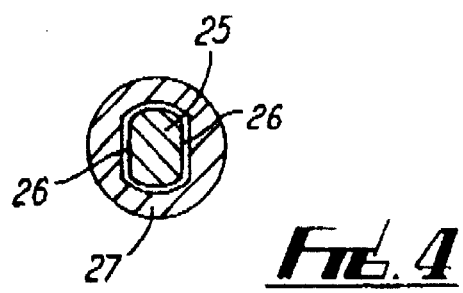
FIG. 4 is a cross-section on line IV—IV of FIG. 3.

As shown in FIGS. 3 and 4, a second embodiment of dental anchoring device comprises a metal rod 21 which is threaded at one end 22.

At its opposite end 23 the rod 21 is shaped, e.g. with 'barb' structures 24, to provide an anchoring part for anchoring a tooth superstructure. At the tip of this end of the rod there is an enlarged head 25 with a flat 26 on one side.

A connecting part 27 in the form of a plastics body (of thermoplastics material) is injection moulded around the end 23 of the rod 21. The body 27 is generally cylindrical (or frusto-conical). It is axially aligned with the rod 21 and has a blind bore 28 which tapers inwardly over part of its length from its open end or receptacle extending axially from the end remote from the rod 21. The body 27 is secured to the rod 21 by the adhesion arising from the injection moulding process and also by the interlocking effect of the enlarged head 25 with the flat 26 and the barbs 24.

In use the anchoring device is attached to a drill bit 29 as shown in FIG. 3 and the threaded end 22 is drilled into a pre-drilled bore in a tooth stump.

When the end 22 is fully inserted the rod 21 automatically separates from the plastics body 27. This arises because the increase in torque causes the plastics material to deform or rupture at its interface with the rod 21 so that there is relative movement between the rod 1 and the plastics body 27 giving rise to the formation of the loose-fitting bore. The plastics body 27 then readily separates from the rod 21. This interface thus comprises a position of weakness in accordance with the present invention. If desired it is also possible to have a further point of weakness in the rod 21.

It is of course to be appreciated that the invention is not intended to be restricted to the details of the above embodiment which are described by way of example only. Thus, for example, in the first embodiment, the diameters of the rods 10, 13 need not be the same. The end of the rod 10 adjacent the position of weakness 14 may have an enlargement if desired. There may be two or more positions of weakness 14. The shapes of the sections 15, 16 and the projections 18 may be different as desired and in accordance with the shape of the bit 1.

What is claimed is:

1. A dental anchoring device comprising a threaded anchoring part, a connecting part including means at a first end of the connecting part for detachable drivable connection to a dentist's drill bit, a second end of the connecting part being attached to the threaded anchoring part, and at least one position of weakness between the anchoring part and the connecting part.

2. A dental anchoring device according to claim 1 wherein the position of weakness is a waisted portion, or a cut-away portion, between the threaded anchoring part and the second end of the connecting part.

3. A dental anchoring device according to claim 2 wherein the threaded anchoring part, the waisted or cut away portion, and the second end of the connecting part adjacent portion are formed in one piece.

4. A dental anchoring device according to claim 3 wherein the means at the first end of the connecting part comprises side abutment faces which engage corresponding side abutment faces of the drill bit to prevent rotation.

5. A dental anchoring device according to claim 2 wherein the means at a first end of the connecting part comprises a receptacle in a body thereof to receive the drill bit, the receptacle comprising an axial bore whereby the body is generally of tubular construction.

6. A dental anchoring device according to claim 2 wherein the means at a first end of the connecting part comprises side abutment faces which engage corresponding side abutment faces of the drill bit to prevent rotation.

7. A dental anchoring device according to claim 1 wherein the position of weakness is a structure which ruptures or deforms circumferentially to permit release of the threaded part when a level of driving torque is exceeded.

8. A dental anchoring device according to claim 7 wherein the rupturable or deformable structure is achieved by drivable interconnection between relatively strong and weak parts, so that the weaker part preferentially ruptures or deforms.

9. A dental anchoring device according to claim 8 wherein the threaded anchoring part comprises a metal rod which is threaded at one end, and the connecting part comprises a plastics body which is moulded around the other end of the rod, said other end of the rod being appropriately configured to drivably key the rod circumferentially to the plastics body.

10. A dental anchoring device according to claim 7 wherein the rupturable or deformable structure is achieved by drivable interconnection between parts which are bonded or welded or similarly fixed together so that the bond or weld or other joint is preferentially ruptured.

11. A dental anchoring device according to claim 7 wherein the means at the first end of the connecting part comprises side abutment faces which engage corresponding side abutment faces of the drill bit to prevent rotation.

12. A dental anchoring device according to claim 1 wherein the means at a first end of the connecting part comprises a receptacle in a body thereof to receive the dentist's drill bit, the body comprising an axial bore whereby the body is generally of tubular construction.

13. A dental anchoring device according to claim 12 wherein the means at a first end of the connecting part for detachable drivable connecting to the dentist's drill bit includes a circumferential locking structure which incorporates elements to prevent rotation relative to the drill.

14. A dental anchoring device according to claim 13 wherein the means at the first end of the connecting part comprises side abutment faces which engage corresponding side abutment faces of the drill bit to prevent rotation.

15. A dental anchoring device according to claim 12 wherein the means at the first end of the connecting part comprises side abutment faces which engage corresponding side abutment faces of the drill bit to prevent rotation.

16. A dental anchoring device according to claim 1 wherein the connecting part has side abutment faces which engage corresponding side abutment faces of the drill bit to prevent rotation.

17. A dental anchoring device according to claim 16, wherein the connecting part has a deflectable abutment structure which makes a releasable snap fit to restrain longitudinal movement relative to the drill.

18. A dental anchoring device comprising a threaded anchoring part, and a connecting part the connecting part including means for detachable drivable connecting to a drill bit engaged in a dentist's drill, the connecting part being drivably interconnected to the anchoring part so as to be releasable therefrom, when a predetermined level of driving torque is exceeded, characterised in that the connecting part is interconnected with the anchoring part by a structure which is adapted to rupture or deform circumferentially to permit said release thereof when said level of driving torque is exceeded.

19. A dental anchoring device according to claim 18 wherein the rupturable or deformable structure is achieved by drivable interconnection between relatively strong and weak parts, so that the weaker part preferentially ruptures or deforms.

20. A dental anchoring device according to claim 18 wherein the rupturable or deformable structure is achieved by drivable interconnection between parts which are bonded or welded or similarly fixed together so that the bond or weld or other joint is preferentially ruptured.

* * * * *